(12) United States Patent
Gevers et al.

(10) Patent No.: US 8,158,824 B2
(45) Date of Patent: Apr. 17, 2012

(54) PROCESS FOR THE PRODUCTION OF UREA FROM AMMONIA AND CARBON DIOXIDE

(75) Inventors: Lambertus Wilhelmus Gevers, Munstergeleen (NL); Jozef Hubert Meessen, Wijlre (NL); Johannes Henricus Mennen, Meijel (NL)

(73) Assignee: Stamicarbon B.V., Sittard (NL)

( * ) Notice: Subject to any disclaimer, the term of this patent is extended or adjusted under 35 U.S.C. 154(b) by 0 days.

(21) Appl. No.: 12/993,824

(22) PCT Filed: May 19, 2009

(86) PCT No.: PCT/EP2009/056068
§ 371 (c)(1),
(2), (4) Date: Mar. 21, 2011

(87) PCT Pub. No.: WO2009/141346
PCT Pub. Date: Nov. 26, 2009

(65) Prior Publication Data
US 2011/0160486 A1    Jun. 30, 2011

(30) Foreign Application Priority Data

May 19, 2008  (EP) .................................... 08156429

(51) Int. Cl.
*C07C 273/04* (2006.01)
(52) U.S. Cl. ................. 564/67; 564/70; 564/71; 564/72
(58) Field of Classification Search ............... 564/67, 564/70, 71, 72
See application file for complete search history.

(56) References Cited

U.S. PATENT DOCUMENTS

| | | | |
|---|---|---|---|
| 2,727,069 A | 12/1955 | Van Waes | |
| 5,767,313 A | 6/1998 | Jonckers | |
| 5,936,122 A | 8/1999 | Kojima et al. | |
| 6,680,407 B2 | 1/2004 | Mennen | |

FOREIGN PATENT DOCUMENTS

| | | |
|---|---|---|
| EP | 0 155 735 | 9/1985 |
| EP | 0 329 215 | 8/1989 |
| EP | 0 834 501 | 4/1998 |
| WO | WO-00/43358 | 7/2000 |

OTHER PUBLICATIONS

International Search Report for PCT/EP2009/056068, mailed on Jul. 7, 2009, 3 pages.

*Primary Examiner* — Peter O Sullivan
(74) *Attorney, Agent, or Firm* — Morrison & Foerster LLP

(57) ABSTRACT

Process for the production of urea from ammonia and carbon dioxide in a urea plant containing a high-pressure synthesis section comprising two reactor sections, a stripper and a condenser, and a recovery section, wherein in the first reactor section a first synthesis solution is formed that is fed to the second reactor section; fresh carbon dioxide is fed to the second reactor section and in the second reactor section a second synthesis solution is formed that is fed to the stripper, wherein the second synthesis solution is stripped with the use of carbon dioxide as stripping gas and the mixed gas stream obtained in the stripper is sent to the condenser together with fresh ammonia and a carbamate stream, whereafter the condensate that is formed in the condenser is fed to the first reactor section and the urea stream that is obtained in the stripper is further purified in the recovery section, wherein the flow of the first synthesis solution from the first reactor section to the second reactor section, the flow of the second synthesis solution from the second reactor section to the stripper, the flow of the mixed gas stream from the stripper to the condenser and of the condensate from the condenser to the first reactor section is a gravity flow.

12 Claims, 2 Drawing Sheets

PROCESS FOR THE PRODUCTION OF UREA FROM AMMONIA AND CARBON DIOXIDE

CROSS-REFERENCE TO RELATED APPLICATIONS

Figure 1:
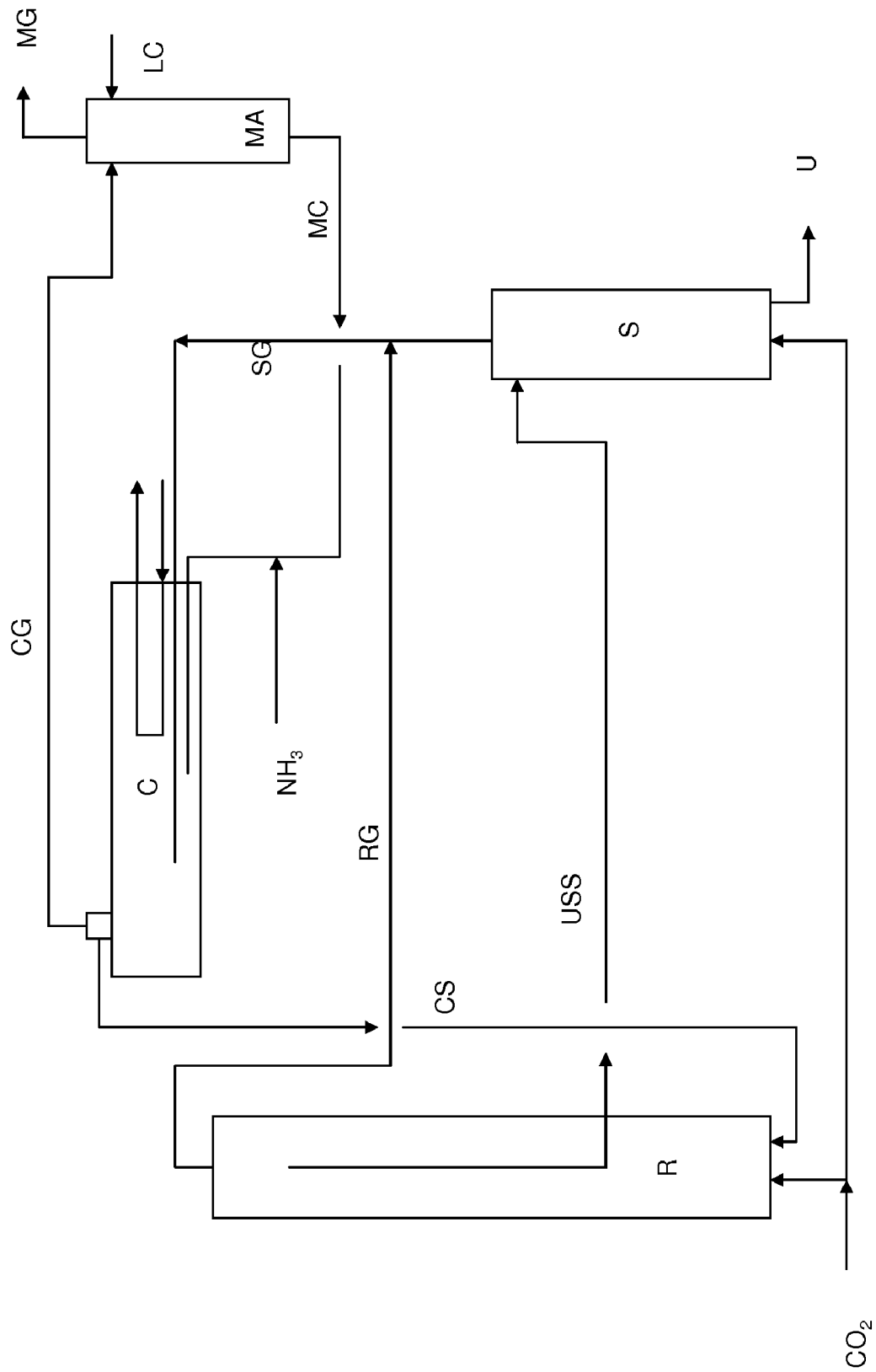

This application is the national phase of PCT application PCT/EP2009/056068 having an international filing date of 19 May 2009, which claims benefit of European application No. 08156429.6 filed 19 May 2008. The contents of the above patent applications are incorporated by reference herein in their entirety.

The invention is directed to a process for the production of urea from ammonia and carbon dioxide in a urea plant containing a synthesis section comprising two reactor sections, a stripper and a condenser, and a recovery section, wherein in the first reactor section a first synthesis solution is formed that is fed to the second reactor section; fresh carbon dioxide is fed to the second reactor section and in the second reactor section a second synthesis solution is formed that is fed to the stripper, wherein the second synthesis solution is stripped with the use of carbon dioxide as stripping gas and the mixed gas stream obtained in the stripper is sent to the condenser together with fresh ammonia and a carbamate stream, whereafter the condensate that is formed in the condenser is fed to the first reactor section and the urea stream that is obtained in the stripper is further purified in a recovery section. An example of such a process for the production of urea is described in U.S. Pat. No. 6,680,407. In this patent a process for the production of urea is described in which the two reactor section sections, the condenser and the scrubber are all combined in one vessel. Because this vessel is used for urea synthesis which takes place at a high-pressure the manufacture of the vessel is expensive and because of the different sections within the vessel it is also very difficult to construct. Moreover a urea plant that contains this vessel is very high.

The object of the invention is to overcome these disadvantages.

The invention is characterized in that the flow of the first synthesis solution from the first reactor section to the second reactor section, the flow of the second synthesis solution from the second reactor section to the stripper, the flow of the mixed gas stream from the stripper to the condenser and of the condensate from the condenser to the first reactor section is a gravity flow.

This has the advantage that a low urea plant can be obtained with two small reactor sections which are easy to place into the construction.

Another advantage is that the process now runs totally on gravity flow for the main recycle of non-converted ammonia and carbon dioxide in the high-pressure synthesis section of the urea production process and the use of energy consuming pumps, compressors or ejectors is superfluous.

In a preferred embodiment of the present invention, the stripper as well as the second reaction section are located on ground level in the plant. In this way, two heavy pieces of equipment are located at a very low elevation in the plant, which results in a considerable reduction of the required investment costs of the structure that has to carry these heavy pieces of equipment. The low location of these pieces of equipment further simplifies the operation and maintenance activities that are required on these equipment items. Also, from a safety point of view, low elevation of heavy pieces of equipment is preferred, since it minimizes the activities of human beings at high level and optimizes safety during construction and operation of the plant.

A process for the production of urea contains a high-pressure synthesis section and one or more recovery sections at lower pressure. The high-pressure section comprises a reactor section in which the urea synthesis solution is prepared, a stripper in which the urea synthesis solution is stripped and a condenser in which the gases released in the stripping zone are condensed.

The synthesis is carried out in two reactor sections. A reactor section is herewith defined as a section wherein at least 20 wt % of the total amount of urea in the synthesis section is formed.

The reactor sections are placed in serial order and can be two separate vessels or two reactor sections placed in one vessel. A reactor section can also be combined with a condenser section in one vessel. When the condenser is a submerged condenser and the residence time in the condenser section is long enough, more than 20 wt % of the total amount of urea is formed in the condenser and it thus functions as a reactor section.

Ammonia and carbon dioxide are fed to the reactor sections either directly or indirectly. Ammonia and carbon dioxide can be introduced to the process for the production of urea at various places in the high-pressure synthesis section or in the recovery sections. Preferably, ammonia is fed to the condenser. Preferably, carbon dioxide is mainly used as a counter-current gas stream during stripping of the urea synthesis solution. A part of the carbon dioxide can be fed to the first or second reactor section.

In the stripper the urea synthesis solution is stripped counter-current with carbon dioxide with the supply of heat. It is also possible to use thermal stripping. Thermal stripping means that ammonium carbamate in the urea synthesis solution is decomposed and the ammonia and carbon dioxide present are removed from the urea solution exclusively by means of the supply of heat. Stripping may also be effected in two or more steps. The gas stream containing ammonia and carbon dioxide that is released from the stripper is sent to a high-pressure condenser. The gas mixture obtained in the stripper is condensed under the removal of heat and absorbed in a high-pressure carbamate condenser, following which the resulting ammonium carbamate is transferred to the reactor section for the formation of urea.

The high-pressure condenser can for example be a falling-film condenser or a so-called submerged condenser as described in NL-A-8400839. The submerged condenser can be placed horizontally or vertically.

In the high-pressure synthesis section the pressure is substantially equal to the urea synthesis pressure in the reactor sections, which is the pressure at which urea formation takes place. The urea synthesis pressure is usually a pressure between 11-40 MPa, preferably 12.5-19 MPa. The pressure in the rest of the high-pressure section is substantially equal to the pressure in the reactor section. Substantially equal means that the pressure in the rest of the high-pressure section is less than 0.5 MPa higher or lower than in the reactor section.

The fact that the flow of the first synthesis solution from the first reactor section to the second reactor section, the flow of the second synthesis solution from the second reactor section to the stripper, the flow of the mixed gas stream from the stripper to the condenser and of the condensate from the condenser to the first reactor section is a gravity flow, means that for this flow no flow-stimulating means are used, like, for instance, pumps, compressors and ejectors.

An oxidizing agent is added to the process for the production of urea in order to protect the materials of construction against corrosion. An oxide skin is formed on the metal parts, which protects against corrosion. This process is known as passivation. The passivating agent may be oxygen or an oxygen-releasing compound as described in for example U.S. Pat. No. 2,727,069. Oxygen can be added, for instance, in the form of air or as a peroxide.

The corrosion sensitive parts in the high-pressure section in the process for the production of urea can be made of a an austenitic-ferritic duplex steel with a chromium content of between 26 and 35 wt. % and a nickel content of between 3 and 10 wt %. This type of steel is less corrosion sensitive. When this type of steel is used for the construction of the reactor sections and the stripper it is possible to reduce or omit the introduction of an oxidizing agent to the process for the production of urea.

Preferably, the chromium content of the austenitic-ferritic duplex steel is between 26-30 wt. %. In the high-pressure section preferably part of the reactor section and the stripper are made of the austenitic-ferritic duplex steel.

In the recovery section ammonia and carbon dioxide that were not removed from the urea synthesis solution in the stripper are recovered from the urea-comprising stream, produced in the high-pressure synthesis section, in order to be recycled to the high-pressure section. In the recovery section the pressure is lower than in the high-pressure synthesis section. In the process for the production of urea according to the present invention at least one low-pressure recovery section is present. When more than one recovery section is present at least one of the recovery sections is operated at medium pressure and one at low pressure. Medium pressure is a pressure between 1.0 and 8.0 MPa, preferably between 1.2 and 3.0 MPa. Low pressure is a pressure between 0.2 and 0.8 MPa, preferably between 0.3 and 0.5 MPa.

The synthesis gas that has not reacted in the second reactor section can be removed from the second reactor section and can be sent to a scrubber, wherein ammonia and carbon dioxide present in the gas flow are removed from the gas flow by absorption in a low-pressure carbamate stream. This carbamate stream is recycled from the low-pressure recovery section of the process for the production of urea. The scrubber can be operated at high-pressure or at medium-pressure. Preferably a medium-pressure scrubber is applied, because a medium-pressure apparatus is cheaper to construct. The scrubbing process in the scrubber can be stimulated by using a heat exchanger that extracts heat from the process. The carbamate stream from the high-pressure scrubber can be returned to the reactor section, optionally via the high-pressure carbamate condenser. The carbamate stream from the medium-pressure scrubber can be returned directly to the first reactor section or can be sent to the first reactor section via the high-pressure carbamate condenser.

The functions of the first and second reactor section, high-pressure carbamate condenser and high-pressure scrubber can be combined in one or two high-pressure vessels, the functionalities of these sections can be separated by baffles designed for small pressure differences in high-pressure vessels.

It is also possible to combine certain functionalities into a single space, without application of separating baffles. An example of such a combination being the combination of the first reactor section with the condenser in a submerged condenser. Such a combination is especially advantageous, both from a cost as well as from an operational point of view, if the heat exchanging function of the condenser is realized in the form of a shell and tube heat exchanger of the U tube type, wherein the high pressure fluid is located on the shell side.

Combination of different sections in one vessel has as a special advantage that substantial savings can be realized in terms of investments, because the amount of high-pressure piping to be installed is much lower. In addition, this increases the reliability of the facility since the number of leakage-sensitive high-pressure connections formed between piping and equipment is greatly reduced. A well-known example is the combination of reactor sections already referred to, as described in U.S. Pat. No. 5,767,313, U.S. Pat. No. 5,936,122 and WO 00/43358. A preferred embodiment is the combination of the pool condenser with a horizontal reactor section as described in U.S. Pat. No. 5,767,313, in which a so-called pool reactor section is represented.

The invention will hereafter be explained in more detail in the examples without being limited thereto.

EXAMPLE I

An example of a process according to the invention is given in FIG. 1. The high-pressure part of the process for the production of urea according to FIG. 1 comprised a second reactor section (R), a $CO_2$ stripper (S) and a submerged condenser/first reactor section (C) that was placed horizontally. Further the process comprised a medium-pressure absorber (MA) and a low-pressure recovery section where the urea stream (U) was further purified.

A small amount of carbon dioxide was fed to the second reactor section (R). In the second reactor section a first urea synthesis solution (CS) was reacted with the carbon dioxide to form a second urea synthesis solution (USS) which was sent to stripper (S) and stripped by the addition of heat and with carbon dioxide as a stripping gas. During stripping a mixed gas stream (SG) was obtained that was, together with reaction gases (RG) coming from the top of the second reactor section (R) fed, via a sparger, to the condenser/first reactor section. To the first reactor section also a carbamate stream (MC) coming from the medium-pressure absorber (MA) was fed together with ammonia. This stream was also fed to the condenser/first reactor section with a sparger. The first urea synthesis solution formed was sent to the second reactor section and the gases that had not been condensed (CG) were sent to the medium-pressure absorber (MA). In the medium-pressure absorber the gases were absorbed in a low-pressure carbamate stream (LC) and condensed. The gases that had not been absorbed (MG) were sent to the low-pressure recovery section. The flow from the USS, SG, and CS was a complete gravity flow. No pumps or ejectors were used to move the fluid or gases.

Of the total amount of urea formed; 65 wt % was formed in the condenser and 35 wt % was formed in the second reactor section.

EXAMPLE II

Figure 2:
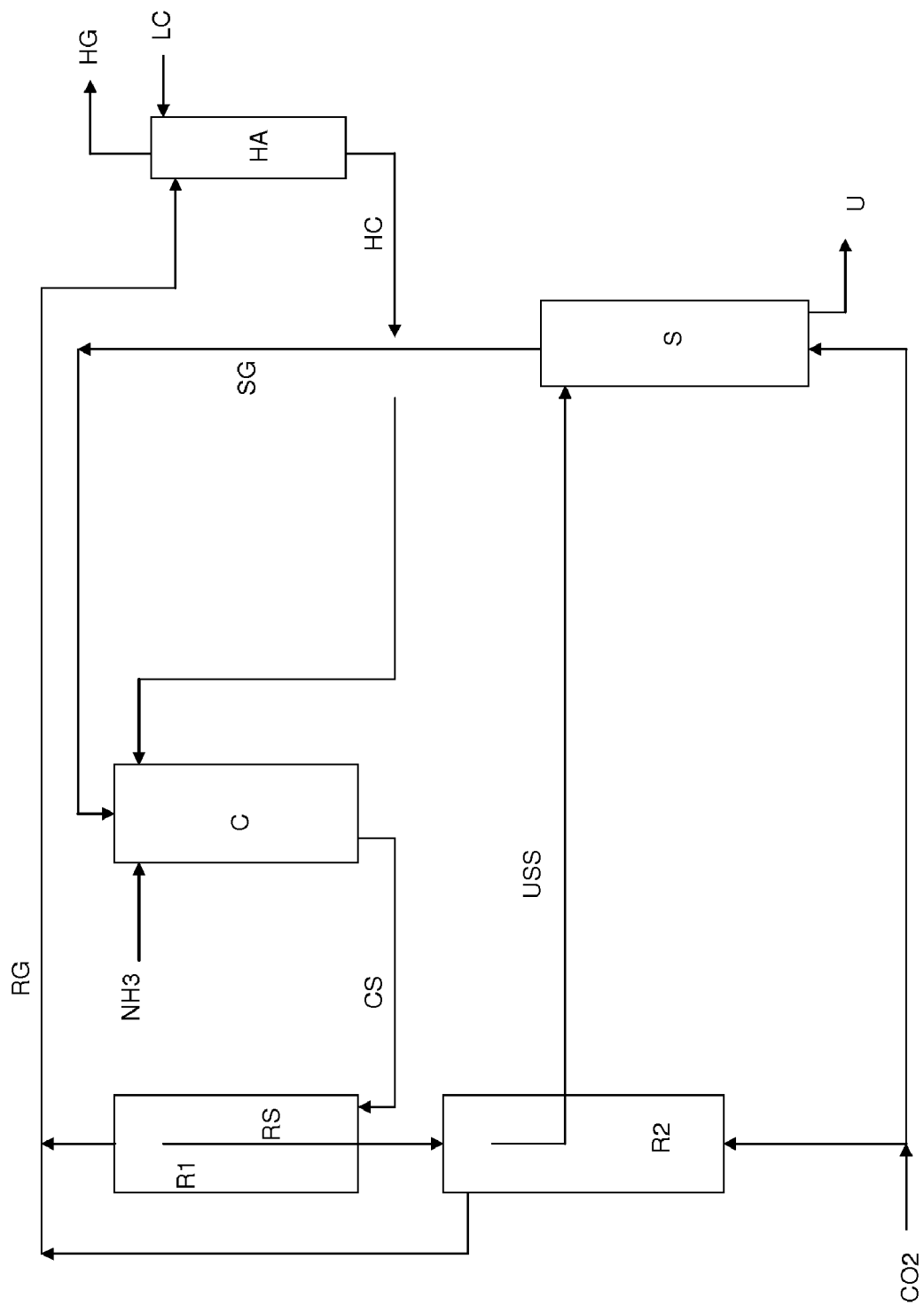

An example of a process according to the invention is given in FIG. 2. The high-pressure part of the process for the production of urea according to FIG. 2 comprised a first and second reactor section (R1 and R2), a $CO_2$ stripper (S), a falling-film condenser (C) and a high-pressure absorber (HA) and a low-pressure recovery section where the urea stream (U) was further purified.

A small amount of carbon dioxide was fed to the second reactor section (R2). In the second reactor section a first urea synthesis solution (RS) coming from the first reactor section (R1) was reacted with the carbon dioxide to form a second urea synthesis solution (USS) which was sent to stripper (S) and stripped by the addition of heat and with carbon dioxide as a stripping gas. During stripping a mixed gas stream (SG) was obtained that was fed to the top of the falling-film condenser (C). To the condenser also a carbamate stream (HC) coming from the high-pressure absorber (HA) was fed and also fresh ammonia.

The carbamate solution (CS) formed was sent to the first reactor section (R1) together with the gases that had not been condensed. Reaction gases (RG) coming from the top of the first and second reactor were sent to the high-pressure absorber (HA). In the high-pressure absorber the gases were absorbed in a low-pressure carbamate stream (LC) and condensed. The gases that had not been absorbed (HG) were sent to the low-pressure recovery section.

The flow from the USS, SG, CS and RS was a complete gravity flow. No pumps or ejectors were used to move the fluid or gases.

Of the total amount of urea formed; 70 wt % was formed in the first reactor section and 30 wt % was formed in the second reactor section.

The invention claimed is:

1. Process for the production of urea from ammonia and carbon dioxide in a urea plant containing a high-pressure synthesis section comprising two reactor sections, a stripper and a condenser, and a recovery section,
   wherein in the first reactor section a first synthesis solution is formed that is fed to the second reactor section; fresh carbon dioxide is fed to the second reactor section;
   and in the second reactor section a second synthesis solution is formed that is fed to the stripper,
   wherein the second synthesis solution is stripped with the use of carbon dioxide as stripping gas and the mixed gas stream obtained in the stripper is sent to the condenser together with fresh ammonia and a carbamate stream,
   whereafter a condensate that is formed in the condenser is fed to the first reactor section and the urea stream that is obtained in the stripper is further purified in the recovery section,
   wherein the flow of the first synthesis solution from the first reactor section to the second reactor section, the flow of the second synthesis solution from the second reactor section to the stripper, the flow of the mixed gas stream from the stripper to the condenser and of the condensate from the condenser to the first reactor section is a gravity flow.

2. Process according to claim 1, wherein both the stripper, and the second reactor section are located at ground level.

3. Process according to claim 1, wherein a gas flow is released from the top of the second reactor section and is sent to a medium-pressure scrubber,
   wherein ammonia and carbon dioxide present in the gas flow are removed from the gas flow by absorption in a low-pressure carbamate stream.

4. Process according to claim 1, wherein the gas flow is released from the top of the second reactor section and is sent to a high-pressure scrubber,
   wherein ammonia and carbon dioxide present in the gas flow are removed from the gas flow by absorption in a low-pressure carbamate stream.

5. Process according to claim 1, wherein a gas flow is released from the top of the first reactor section and the top of the second reactor section and combined and the combined gas flow of the both reactor sections is sent to a medium-pressure scrubber or a high-pressure scrubber,
   wherein ammonia and carbon dioxide present in the combined gas flow are removed from the gas flow by absorption in a low-pressure carbamate stream.

6. Process according to claim 1, wherein the first reactor section and the second reactor section are combined in one vessel.

7. Process according to claim 1, wherein the first reactor section and the condenser are combined in one vessel.

8. Process according to claim 7, wherein the vessel is placed horizontally.

9. Process according to claim 1, wherein the condenser is submerged and placed horizontally.

10. Process according to claim 9, wherein the submerged condenser is of the shell and tube type and that high pressure fluids are on the shell side.

11. Process according to claim 10, wherein the shell and tube type heat exchanger is of the U-tube type.

12. Process according to claim 1, wherein at least part of the reactor or stripping sections is made of an austenitic-ferritic duplex steel with a chromium content of between 26 and 35 wt. % and nickel content of between 3 and 10 wt. %.

* * * * *